US00PP28242P3

(12) United States Plant Patent
Villegas

(10) Patent No.: US PP28,242 P3
(45) Date of Patent: Aug. 1, 2017

(54) ***SANSEVIERIA* PLANT NAMED 'BLACK LIMÓN'**

(50) Latin Name: *Sansevieria trifasciata*
Varietal Denomination: Black Limón

(71) Applicant: FLORICA FARMS, INC., Eustis, FL (US)

(72) Inventor: Marvin Gonzalez Villegas, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 79 days.

(21) Appl. No.: 14/756,628

(22) Filed: Sep. 28, 2015

(65) Prior Publication Data

US 2017/0094876 P1 Mar. 30, 2017

(51) Int. Cl.
*A01H 5/00* (2006.01)

(52) U.S. Cl.
USPC ..... Plt./382

(58) Field of Classification Search
USPC ..... Plt./382
CPC ..... A01H 5/00
See application file for complete search history.

*Primary Examiner* — Kent L Bell
(74) *Attorney, Agent, or Firm* — Foley & Lardner LLP

(57) ABSTRACT

The new variety Black Limón is part of the "long leaves" group of *Sansevieria* varieties and is a naturally-occurring mutation of the *Sansevieria trifasciata* variety 'Laurentii'. It can reach 50-80 cm in length, with an average of approximately 3-5 leaves per plant. The plant is cylindrically shaped, with an erect growth habit and the arrangement of the leaves is in the form of a rosette. The new variety shows coloration very different from its parent variety and has variegated green leaves with light yellow-green colored margins. The new variety needs little water and is very drought tolerant.

3 Drawing Sheets

Figure 1:
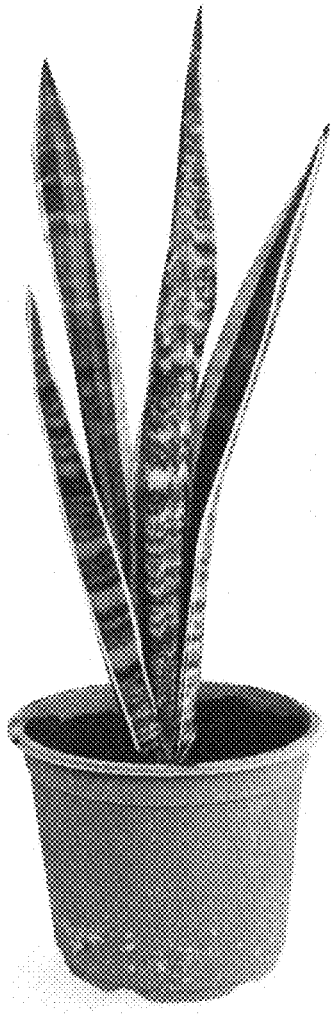

Latin name of the genus and species of the claimed plant: *Sansevieria trifasciata.*

Variety denomination: Black Limón.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Black Limón'.

*Sansevieria* is a monocotyledonous and succulent, flowering plant which can be produced in either hard-leafed or soft-leafed varieties for interior use as a house plant or outdoor ornamental plant.

The new variety 'Black Limón' originated as a naturally-occurring mutation of the *Sansevieria trifasciata* variety 'Laurentii' (unpatented). The new *Sanseviera* 'Black Limón' was discovered and selected by the inventor, Marvin Gonzalez Villegas, as a single sprouting rare mutated plant in a plantation of *Sansevieria trifasciata* 'Laurentii', a controlled environment, in 2012 in Monterrey, San Carlos, Alajuela province, Costa Rica.

Asexual reproduction of the new *Sansevieria* cultivar 'Black Limón' by vegetative cuttings was first performed in 2012 in Monterrey, San Carlos, Alajuela province, Costa Rica and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Black Limón', which in combination distinguish this *Sansevieria* as a new and distinct cultivar:

1. Variegated foliage with different green tones on the irregular bands, and light green colored margin bands in the leaf blade
2. Wide and lanceolate leaves, supported in a rosette.
3. 50-80 cm plant height.
4. Erect plant habit
5. Needs little water and is very drought tolerant.

The new variety 'Black Limón' is considered a variety of "long-leaves" *Sansevieria*. The new variety presents an average of 3-5 leaves per plant when it reaches its maturity (between 8-12 months). The new variety has an erect growth habit and the entire plant can reach a height range between 50-80 cm. The leaves are narrow (3-5 cm average measured at the widest part of the mature leaf) and lanceolate, with a soft waxy texture. The blades are thin and slightly wavy. The plant has a cylindrical shape.

The new variety is very drought tolerant, adapts to conditions of light and shade (interior and exterior), and shows high tolerance level to antrachnose (*Colletotrichum sansvierae*) disease.

The leaf blade is dark green colored (RHS 134A), with non-uniform horizontal variegated bands in both sides of the leaves, moderate green (RHS 140B) colored, and also presents broad longitudinal light yellow-green (RHS149A) colored margins.

The variety 'Laurentii' gave rise to the variety 'Black Limón'. The parent variety 'Laurentii' is also considered a "long-leaves" *Sansevieria*. 'Laurentii' shows a little more vigor than 'Black Limón', has a higher number of leaves per plant (5-6), with an average width of 4-6 cm (measured in the middle of the mature leaf.) The growth habit is erect and presents narrow leaves supported in a rosette. The entire plant can reach a size between 60-90 cm. The plant has, as for 'Laurentii', a cylindrical shape.

Plants of the new *Sansevieria* 'Black Limón' differ from plants of the parental cultivar, 'Laurentii' (unpatented) in the characteristics described in Table 1.

TABLE 1

Comparison between new cultivar 'Black Limón' and its parent variety 'Laurentii'.

| Characteristic | New Cultivar 'Black Limón | Parent Cultivar 'Laurentii' (unpatented) |
|---|---|---|
| Plant Vigor | less vigorous (less leaves) | more vigorous (more leaves) |
| Color | variegated leaves (different green tones on the irregular bands) and light greenish colored stripes along the margins | variegated leaves (different green tones on the irregular bands) and light yellow colored stripes along the margins |
| Shape | 3-5 cm wide and lanceolated leaves on a rosette | 4-6 cm wide and lanceolated leaves on a rosette |
| Texture of leaves | smooth-textured leaves | smooth-textured leaves |

Of the many commercial cultivars known to the present inventor, the most similar in comparison to the new *Sansevieria* 'Black Limón' is the *Sansevieria* 'Laurentii'.

BRIEF DESCRIPTION OF THE PHOTOGRAPHS

The accompanying photographs illustrate the overall appearance of the new *Sansevieria* cultivar 'Black Limón' showing the colors as true as is reasonably possible with colored reproductions of this type. Colors in the photographs may differ slightly from the color value cited in the detailed botanical description which accurately describe the color of 'Black Limón'.

FIG. 1—Shows a side view of an eight-month old plant of *Sansevieria* 'Black Limón' in a 21 cm diameter pot.

Figure 2:
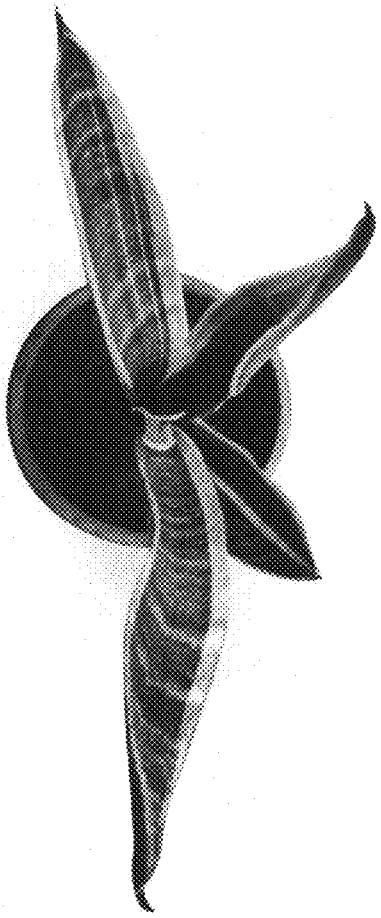

FIG. 2—Shows a top-down view of an eight-month old typical plant of 'Black Limón'.

Figure 3:
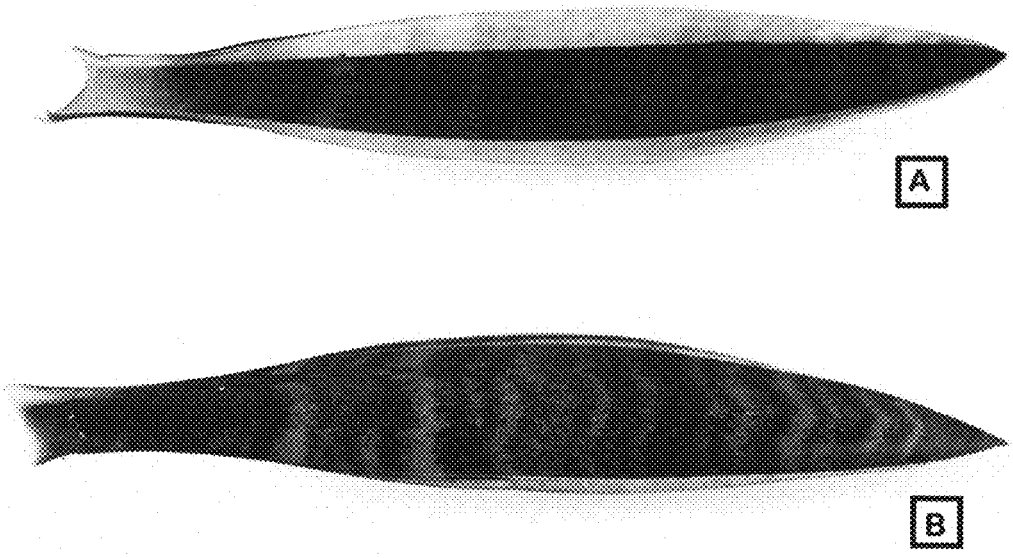

FIG. 3—shows a close-up view of typical leaves of 'Black Limón' from an eight-month old plant (upper side in A, under side in B).

DETAILED BOTANICAL DESCRIPTION

The new *Sansevieria* 'Black Limón' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'Black Limón' as grown in open-field conditions at Monterrey, San Carlos, Alajuela province, Costa Rica, under conditions which closely approximate those generally used in commercial practice. 24.5° C. during the day and 18° C. at night. Plants grow under natural light conditions.

This crop does not require constant fertilization, to increase production per area about 200 kg ha−1 N, 150 kg ha−1 of P and 100 kg ha−1 K are required, the production is closely related with soil conditions in which they are grown.

Color references are made to The Royal Horticultural Society Colour Chart Edition V, version 2, except where general colors of ordinary significance are used. The photographs and descriptions were taken during the rainy season in Monterrey, San Carlos, Alajuela province, Costa Rica when outdoor day temperature was 23° C. The age of the plants described is 8 months.

Classification:

*Botanical.*—*Sansevieria trifasciata.*

*Variety denomination.*—'Black Limón'.

Parentage: *Sansevieria trifasciata* 'Laurentii' (unpatented).

Optimal growth conditions:

*Light intensities.*—High adaptability to outdoor or indoor conditions.

*Temperature.*—Day: 24° C. to32° C. Night: 18° C. to 23° C.

*Temperature tolerance.*—Tolerant to temperatures between 12° C. and 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit description.*—Rhizomes, with short roots.

*Time to initiate roots.*—15 to 22 days at 20-25° C.

*Faster time to produce a rooted cutting.*—About 60 to 90 days at 20-25° C.

Plant:

*General appearance and form.*—

*Height.*—About 80 cm when grown in ground; about 50 cm when grown in a 21 cm size container.

*Spread.*—About 15 cm when grown in ground; About 10 cm when grown in 21 cm size container.

*Form.*—Monocot; leaf bases arranged in a rosette around growth point.

*Shape.*—Cylindrical.

*Growth rate and habit.*—About 2.5 cm per week; erect.

*Fragrance.*—None.

*Stem.*—Modified (Rhizome and foliage). Length: About 12 cm when grown in ground; About 8 cm when grown in 21cm size container. Diameter: About 1.8-2.0 cm. Shape: Round. Texture: Rough. Color: RHS 17A, Yellow-Orange. Strength: Strong and durable. Internode length: About 0.5 mm to 0.7 mm.

Foliage:

*Quantity.*—About 3-5 leaves.

*Arrangement and attachment.*—Single, alternate; leaf bases arranged in a rosette around growth point.

*Leaf length.*—About 65 cm.

*Leaf width.*—About 3-5 cm.

*Overall shape of leaf.*—Lanceolated.

*Apex shape.*—Acute, triangular.

*Base shape.*—Plane.

*Margin.*—Sharp, smooth.

*Texture.*—Upper Surface: smooth and waxy texture. Under Surface: smooth and waxy texture.

*Pubescence.*—None.

*Color (mature and immature leaves; upper and lower surfaces).*—Leaf Blade RHS 134A Green, with non-uniform horizontal variegated bands of RHS 140B Green, and margins RHS149A Yellow-Green. Margin coloration wider on upper surface (1.0 cm) vs. lower surface (0.5 cm).

*Venation.*—None.

*Leaf fragrance.*—None.

Inflorescence description:

*Arrangement and type.*—Inflorescence.

*Orientation at opening.*—Out of the spike.

*Quantity.*—Per Plant with at least one open flower: About 20 at 2 weeks.

*Inflorescence size*.—Length: About 30 cm. Diameter: About 0.4 cm.

*Flower size*.—Length: About 28 cm. Diameter: About 0.5 cm. Depth: About 1 cm.

*Fragrance*.—None.

*Buds*.—

*Rate of opening*.—About 7 to 8 days, according to weather.

*Shape*.—Ovoid.

*Length*.—About 3 cm.

*Diameter*.—About 1 cm.

*Color*.—Apex: RHS 149 B, Yellow-green. Base: RHS 142 B, Green.

*Texture* (*both surfaces*).—Smooth.

Petals:

*Quantity*.—6.

*Arrangement*.—Star-shaped.

Reproductive organs:

*Androecium*.—Stamen: Number: 5 per flower. Length: About 1.2 cm. Color: RHS 149B, Yellow-green. Anther: Length: About 2 mm. Width : About 1 mm. Color: RHS 149B, Yellow-green. Filament: Length: About 1.3 cm. Color: RHS 149B, Yellow-green. Pollen: Amount: moderate. Color: RHS 149B, Yellow-green.

*Gynoecium*.—Pistil: Number: One per flower. Length: About 2.0 cm. Stigma: Length: About 0.6 mm. Width: About 1 mm. Color: RHS 149B, Yellow-green. Style: Length: About 2.2 cm. Color: RHS 149B, Yellow-green. Ovary: Length: About 4 mm. Width: About 2 mm. Color: RHS 149B, Yellow-green.

Weather resistance: Very drought tolerant.

Disease/pest resistance: High tolerance to antrachnose (*Colletotrichum sansevierae*).

Disease/pest susceptibility: Not observed.

I claim:

1. A new and distinct *Sansevieria* plant named 'Black Limón', substantially as illustrated and described herein.

* * * * *